US00PP29168P3

(12) United States Plant Patent
Howell

(10) Patent No.: US PP29,168 P3
(45) Date of Patent: Apr. 3, 2018

(54) APPLE TREE NAMED 'HOWELL TC4 WF'

(50) Latin Name: *Malus Domestica*
Varietal Denomination: Howell TC4 WF

(71) Applicant: William Edward Howell, Prosser, WA (US)

(72) Inventor: William Edward Howell, Prosser, WA (US)

( * ) Notice: Subject to any disclaimer, the term of this patent is extended or adjusted under 35 U.S.C. 154(b) by 0 days.

(21) Appl. No.: 15/530,419

(22) Filed: Jan. 10, 2017

(65) Prior Publication Data

US 2017/0202120 P1 Jul. 13, 2017

Related U.S. Application Data

(60) Provisional application No. 62/388,025, filed on Jan. 12, 2016.

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette H Para
(74) *Attorney, Agent, or Firm* — Michelle Bos Legal LLC

(57) ABSTRACT

A new and distinct apple tree is disclosed. 'Howell TC4 WF' is notable for its fruit, which has distinctive pinkish-red skin and sweet/tart flavor.

3 Drawing Sheets

Latin name of the genus and species of the plant claimed: *Malus Domestica.*
Variety denomination: 'Howell TC4 WF'.

CROSS-REFERENCE TO RELATED APPLICATIONS

None.

STATEMENT REGARDING FEDERALLY SPONSORED RESEARCH OR DEVELOPMENT

None.

BACKGROUND OF THE INVENTION

The new variety of apple tree 'Howell TC4 WF' was created in the course of a planned breeding program carried out in Prosser, Wash. 'Howell TC4 WF' originated as a result of an open pollination cross in 2001 of 'Cripps Pink' (U.S. Plant Pat. No. 7,197, expired), seed parent, with the pollen parent being 'Honeycrisp' (U.S. Plant Pat. No. 7,197, expired). 'Howell TC4 WF' was selected in 2010 as a single plant from among a population of seedlings derived from the parents, and was selected for its quality of fruit. It is distinguished from its parents by its bicolored pinkish-red skin and by its flavor. Asexual propagation by budding was first carried out in Prosser, Wash. The variety has since been observed over a number of asexually propagated generations, and has been found to remain true to type.

BRIEF SUMMARY OF THE INVENTION

'Howell TC4 WF' is a new and distinct apple tree notable for its distinctive fruit, which has pinkish-red bicolored skin and a sweet/tart flavor.

BRIEF DESCRIPTION OF THE PHOTOGRAPH

Figure 1:
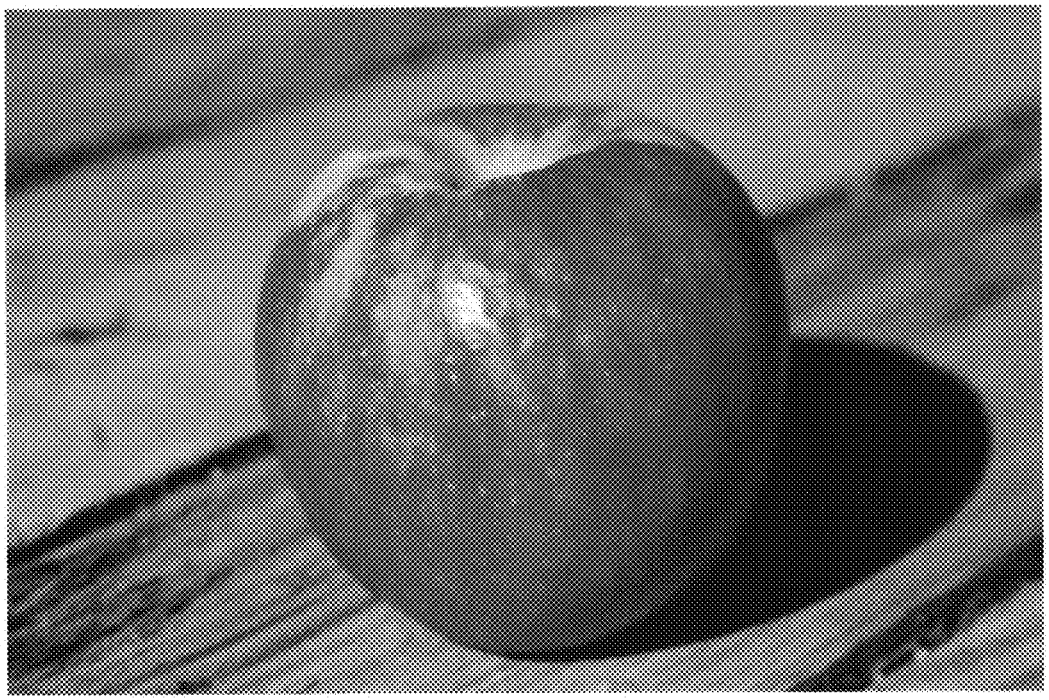
Figure 2:
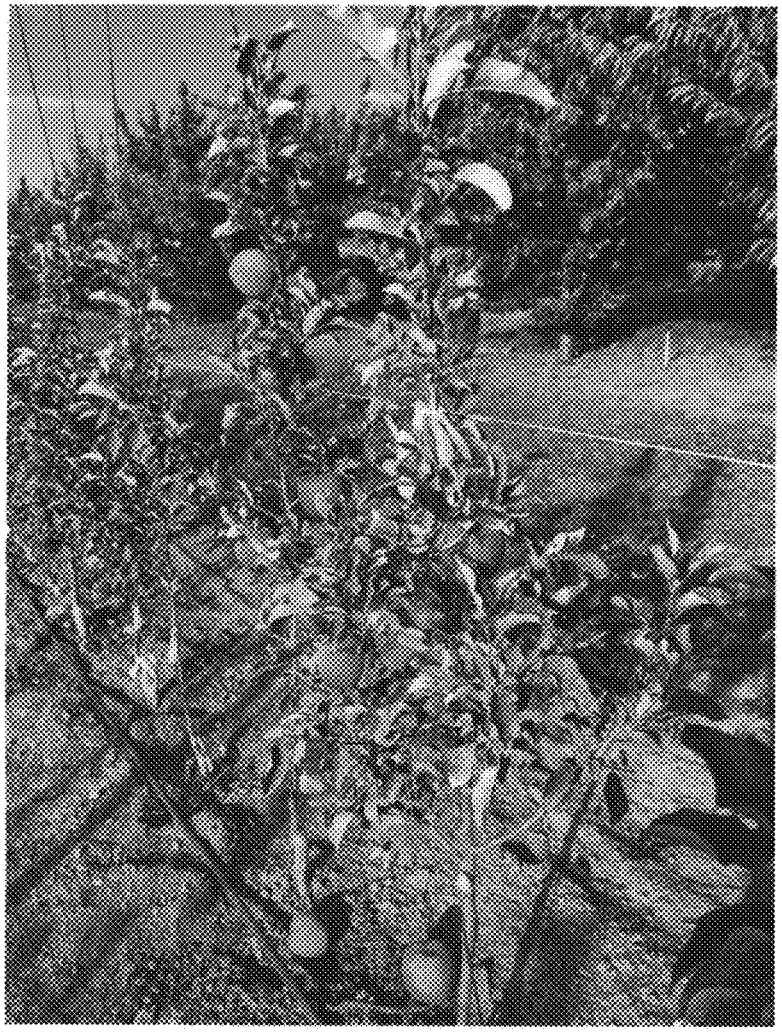
Figure 3:
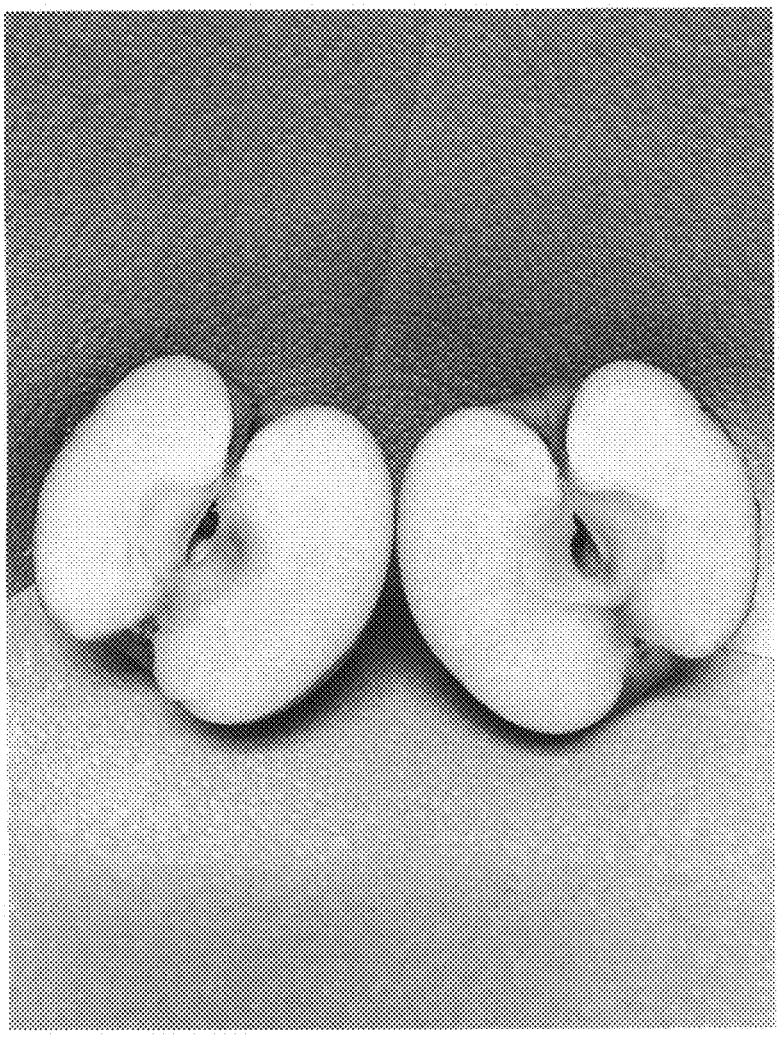

FIG. 1 shows the fruit of the claimed variety;
FIG. 2 shows a tree of the claimed variety; and
FIG. 3 shows a sectioned fruit of the claimed variety.

DETAILED BOTANICAL DESCRIPTION

The following detailed botanical description is based on observations made during the 2015 growing season at Prosser, Wash. All colors are described according to The Royal Horticultural Society Colour Chart as published in 2001. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor.*—Semi-vigorous.
- *Size.*—Height 2.7 m, spread 1.2 m.
- *Trunk.*—2.5 cm diameter at 30 cm above graft union.
- *Bark texture.*—Smooth.
- *Bark coloration.*—Gray to reddish-brown.

Branch:
- *Size.*—Length 81.3 cm; diameter 1.27 cm at 1 m above ground.
- *Crotch angle relative to trunk.*—60°.
- *Color.*—Gray to reddish-brown.

Dormant one-year-old shoot:
- *Length.*—62 cm.
- *Diameter.*—0.5 cm.
- *Color.*—Greyed-orange 165A.
- *Internode length.*—3 cm.
- *Lenticel size.*—Diameter 0.5 mm.
- *Lenticel color.*—White 155C.
- *Quantity.*—12 per cm2.

Flowers:
- *Bud quantity per spur.*—5.
- *Bud shape.*—Conic.

*Bud length.*—1 cm.
*Bud diameter.*—0.7 cm.
*Bud color.*—Greyed-purple 186B.
*Color at balloon stage.*—Greyed-purple 186C with white N155D in the middle.
*Diameter of open flower.*—4.5 cm.
*Petal quantity per flower.*—5.
*Margin.*—Smooth.
*Relative position of petal margin.*—Touching.
*Petal length.*—2 cm.
*Petal width.*—1.6 cm.
*Apex shape.*—Round.
*Base shape.*—Pointed.
*Color of upper surface.*—White N155D with greyed-purple 186D.
*Color of lower surface.*—White N155D with greyed-purple 186C.
*Pistil size.*—1 cm.
*Pistil color.*—Yellow-green 145D.
*Anther quantity.*—14.
*Size.*—0.1 cm.
*Color of pollen.*—Yellow 2C.
*Stigma size.*—0.1 cm.
*Stigma color.*—Yellow 1C.
*Style size.*—1 cm.
*Style color.*—Yellow 1D.
*Ovary width.*—0.3 cm.
*Ovary length.*—0.5 cm.
*Ovary color.*—Yellow-green 146B.
*Bloom period.*—First bloom March 25, full bloom April 3 in Prosser, Wash.
*Pedicel length.*—1.5 cm.
*Pedicel diameter.*—0.2 cm.
*Pedicel color.*—Yellow-green 145B.

Sepals:
*Quantity.*—5.
*Color.*—Yellow-green 145B.
*Length.*—0.6 cm.
*Width.*—0.3 cm.

Leaf:
*Shape.*—Aristate.
*Attitude in relation to shoot.*—30° angle off stem.
*Blade margin.*—Serrated.
*Apex.*—Pointed.
*Base shape.*—Rounded.
*Length.*—9 cm.
*Width.*—6 cm.
*Color of upper surface.*—Yellow-green 146A.
*Color of lower surface.*—Yellow-green 146C.
*Petiole length.*—4 cm.
*Petiole color.*—Yellow-green 146C.

Fruit:
*Size.*—Diameter 7.7 cm, height 7.6.
*Weight.*—204 g.
*General shape in profile.*—Rounded.
*Ribbing.*—Absent.
*Crowning at calyx end.*—Absent.
*Size of eye.*—Diameter 2.5 cm.
*Stalk.*—Length 2.5 cm, width 0.3 cm.
*Depth of stalk cavity.*—1 cm.
*Width of stalk cavity.*—2 cm.
*Size of lenticels.*—0.1 cm.
*Ground color of skin.*—Yellow-green 154C.
*Over color of skin.*—Red 46B.
*Pattern of over color.*—Blush.
*Flesh.*—Crisp and juicy.
*Flesh color.*—White 155A.
*Stem color.*—Yellow-green 145A.
*Quantity of seeds.*—6 per fruit.
*Shape of seed.*—Acuminate.
*Seed length.*—0.7 cm.
*Seed width.*—0.4 cm.
*Seed color.*—Greyed-orange 163A.

Harvest timing: Last week of September in Prosser, Wash.
Disease resistance/susceptibility: None noted.
Use: Fresh Market and processing.

I claim:

1. A new and distinct apple tree substantially as shown and described herein.

* * * * *